United States Patent
Sournac et al.

(10) Patent No.: US 9,358,051 B2
(45) Date of Patent: Jun. 7, 2016

(54) SYSTEM FOR RETAINING AN ANCHORING MEMBER ON AN IMPLANTABLE PART

(75) Inventors: Denys Sournac, Reyrieux (FR); David Ryan, Collonges au Mont d'Or (FR)

(73) Assignee: MEDICREA INTERNATIONAL, Neyron (FR)

( * ) Notice: Subject to any disclaimer, the term of this patent is extended or adjusted under 35 U.S.C. 154(b) by 143 days.

(21) Appl. No.: 13/695,727

(22) PCT Filed: May 17, 2011

(86) PCT No.: PCT/IB2011/052151
§ 371 (c)(1),
(2), (4) Date: Nov. 1, 2012

(87) PCT Pub. No.: WO2011/145047
PCT Pub. Date: Nov. 24, 2011

(65) Prior Publication Data
US 2013/0053967 A1     Feb. 28, 2013

(30) Foreign Application Priority Data

May 17, 2010 (FR) .................................. 10 53800
Dec. 16, 2010 (FR) .................................. 10 60660

(51) Int. Cl.
*A61F 2/44* (2006.01)
*A61B 17/80* (2006.01)
(Continued)

(52) U.S. Cl.
CPC ............. *A61B 17/8047* (2013.01); *A61F 2/447* (2013.01); *A61B 17/86* (2013.01); *A61F 2002/30443* (2013.01); *A61F 2002/4475* (2013.01)

(58) Field of Classification Search
CPC ...................... A61B 17/8033–17/8047; A61B 17/70–17/7046; A61B 17/80–17/8095; A61B 17/84–17/8695
USPC .......................................... 606/280–299, 319
See application file for complete search history.

(56) References Cited

U.S. PATENT DOCUMENTS 6,022,350 A * 2/2000 Ganem .......................... 606/272
7,311,712 B2 * 12/2007 Dalton ............................ 606/71
(Continued)

FOREIGN PATENT DOCUMENTS

FR      2 861 980 A1    5/2005
FR      2 861 980 B1    9/2006

OTHER PUBLICATIONS

Jul. 21, 2011 International Search Report issued in Application No. PCT/IB2011/052151.
(Continued)

*Primary Examiner* — Jan Christopher Merene
*Assistant Examiner* — Steven Cotroneo
(74) *Attorney, Agent, or Firm* — Oliff PLC (57) ABSTRACT

This system includes a retaining housing formed by a hole intended to receive the anchoring member and a retaining portion arranged on the anchoring member; said retaining housing is arranged in a part having a degree of elastic flexibility and is delimited by a continuous wall of this part; the retaining housing, on the side of a first axial end, forms a first collar forming a continuous circular projection capable of being elastically deformed by the retaining portion arranged on the anchoring member; the wall of said part delimiting the retaining housing also forms, on a second axial end, a second collar not able to be elastically deformed by said retaining portion.

10 Claims, 5 Drawing Sheets

(51) Int. Cl.
*A61B 17/86* (2006.01)
*A61F 2/30* (2006.01)

(56) References Cited

U.S. PATENT DOCUMENTS

| | | | | |
|---|---|---|---|---|
| 7,766,947 | B2* | 8/2010 | Hawkes et al. | 606/280 |
| 7,896,902 | B2* | 3/2011 | Jeon et al. | 606/246 |
| 2003/0149432 | A1* | 8/2003 | Frigg et al. | 606/61 |
| 2003/0153912 | A1* | 8/2003 | Graf | 606/61 |
| 2004/0087951 | A1 | 5/2004 | Khalili | |
| 2005/0033298 | A1* | 2/2005 | Hawkes et al. | 606/61 |
| 2005/0203516 | A1* | 9/2005 | Biedermann et al. | 606/61 |
| 2006/0235399 | A1* | 10/2006 | Carls et al. | 606/69 |
| 2007/0118123 | A1* | 5/2007 | Strausbaugh et al. | 606/61 |
| 2007/0233087 | A1* | 10/2007 | Schlapfer | 606/61 |

OTHER PUBLICATIONS

Jul. 21, 2011 Written Opinion of the International Searching Authority issued in Application No. PCT/IB2011/052151.

* cited by examiner

SYSTEM FOR RETAINING AN ANCHORING MEMBER ON AN IMPLANTABLE PART

The present invention concerns a system for retaining an anchoring member on an implantable part associated with this anchoring member.

The applications of the invention of particular interest are spinal applications for retaining an anchor screw relative to a vertebral plate used to immobilise two or three adjacent vertebrae with each other, or to retain an anchor screw relative to an intervertebral cage.

Some pathologies affecting the vertebrae or the intervertebral discs require two or three adjacent vertebrae to be immobilised together. This immobilisation is frequently achieved by means of metal plates placed on the anterior or lateral faces of the vertebral bodies which are fastened to these vertebral bodies via screws engaged through holes provided in these plates. Such immobilisation is also frequently achieved by means of an intervertebral cage intended to be inserted between the bodies of two vertebrae, fastened to these vertebrae via screws engaged through the holes provided therein.

The major disadvantage of said fixing screws is that they risk becoming unscrewed under the effect of micro-movements and repeated stresses exerted thereupon by the vertebrae, especially as the bone of the vertebrae concerned does not necessarily allow anchoring of very good quality (the case with elderly patients) or if the dimensions of the vertebrae concerned do not offer a sufficiently large anchor surface (in particular in the treatment of cervical vertebrae).

To overcome this disadvantage, various means have been designed for retaining a screw on a plate, in particular in the form of bushings or split rings intended to be expanded by the screw, split rings of "circlips" type, screwable plates which cover the head of one or more screws, or portions of the material of the plate forming flaps over the head of a screw.

Existing systems have the disadvantage either of not ensuring perfect retaining of the screws relative to the plate, or they involve an additional procedural step for fastening thereof, for example screwing of the above-mentioned plates, or they do not allow the screw to be oriented relative to the plate in the most suitable anchoring direction.

It is the objective of the present invention to overcome all these disadvantages.

Document US 2006/235399 describes a ring having a slit over its entire thickness, hence intended to undergo radial expansion, and which does not ensure axial retaining of the screw. The technical solution described in this document does not overcome the aforementioned disadvantages in satisfactory manner.

Document US 2004/087951 describes an elastic split ring of conical shape, housed in an upper conical housing provided in the vertebral plate, this housing having larger dimensions than the ring and surmounting a semi-spherical lower housing. This ring, when the maximum diameter of the spherical head has advanced beyond it, is moved upwardly by sliding along the head of the screw under elastic return until the outer peripheral surface of the ring comes to be applied against the conical peripheral wall of the conical housing containing the ring. The technical solution described by this document is complex, appears difficult and very costly to implement in practice, and therefore does not allow the aforementioned disadvantages to be satisfactorily remedied.

The retaining system to which the invention applies comprises:
- a retaining housing formed by the peripheral surface of the hole intended to receive the anchoring member, having a first diameter at a first axial end, which is the end via which the anchoring member is intended to be inserted through this retaining housing, and a second diameter, smaller than the said first diameter, at the second axial end thereof; and
- a retaining portion arranged on the anchoring member, intended to be located at said retaining housing once the anchoring member has been placed in position;
- the retaining housing is arranged in a part having a degree of elastic flexibility and is delimited by a continuous wall of this part;
- the retaining housing, between said first diameter and second diameter, has a maximum diameter that is larger than said first diameter and second diameter; the wall of said part delimiting the retaining housing, on the side of said first axial end, therefore forms a first collar integral with said part, forming a continuous circular projection whose dimensions are such that this first collar is capable of being elastically deformed by the retaining portion arranged on the anchoring member; the wall of said part delimiting the retaining housing also forms, on the side of said second axial end, a second collar whose dimensions are such that this second collar is not able to be elastically deformed by said retaining portion;
- this retaining portion provided in the anchoring member has a maximum diameter that is substantially identical to said maximum diameter of said retaining housing, and is shaped so that it is able to follow the contour of this housing when the anchoring member is placed in position, said retaining portion therefore being capable of elastically deforming said first collar then of taking up a position in fitted manner inside the retaining housing, bearing against said second collar which it is not able to deform; and
- said part having a degree of elastic flexibility is an elastically deformable material, which degree of deformability is sufficient to allow, by elastic deformation, the passage of said retaining portion beyond said first collar.

The invention therefore provides a retaining system comprising a retaining housing arranged in a part made of a single material and having a degree of elastic flexibility; this housing forms a proximal collar able to be deformed by the retaining portion provided in the anchoring member, and it is sized so as to receive this spherical retaining portion in fitted manner once it has advanced beyond said proximal collar. With this system it is therefore possible to ensure perfect retaining of the anchoring member relative to the implantable part, and to achieve said elastic deformation it does not involve any additional surgical act other than the placing in position of the anchoring member on the implantable part.

Preferably, said part having a degree of elastic flexibility is in a material that is elastically slightly deformable and whose degree of deformability is sufficient to enable the passing, by elastic deformation, of said retaining portion beyond said first collar.

This material that is elastically slightly deformable may, in particular, be PEEK material (polyetheretherketone).

If necessary, and depending on the material used for this part and the thickness thereof, this part could comprise in its proximal portion a series of notches delimiting teeth between them that are elastically mobile in the radial direction.

According to one possible embodiment of the invention, said retaining housing is arranged directly in the wall of said implantable part.

Said part having a degree of elastic flexibility is then said implantable part itself.

According to another possible embodiment of the invention:

said retaining housing is arranged in a circular ring with a continuous peripheral wall, whose outer peripheral surface is in the shape of a sphere segment containing the equator of this sphere;

a housing is arranged in said implantable part to receive the ring, this housing being shaped as a sphere segment containing the equator of this sphere, and having a diameter such that the ring is capable of taking up position in fitted manner inside the housing and of being retained inside the housing with possible multidirectional movements of this ring inside this housing.

Said part having a degree of elastic flexibility in this case is formed by said ring. The above-mentioned maximum diameter, on the side of said first axial end of the ring, defines a proximal portion of the ring whose mean radial thickness is smaller than the mean radial thickness of the distal portion of this ring, since said first diameter is greater than said second diameter. This smaller radial thickness enables said proximal portion to allow the forced passing of said retaining portion of the anchoring member beyond the first collar until this retaining portion is received and retained in the housing defined by the inner peripheral surface of the ring; the distal portion of the ring, on account of its greater mean radial thickness than at the proximal portion of this ring, forms said second collar which is rigid and therefore prevents the passing beyond it of said retaining portion of the anchoring member.

Preferably, said retaining housing and said retaining portion have spherical shapes.

The arrival of said retaining portion in position in the housing formed by said retaining housing allows the anchoring member to be oriented relative to the implantable part in the most suitable anchoring direction, by means of the multidirectional mobility of this anchoring member in said housing.

Preferably, in this case, the aforementioned maximum diameter is the equator of the sphere segment defining the retaining housing, and this equator is offset along the axis of the retaining housing on the side of the said first end.

According to one possibility, said first end of the retaining housing is extended by a wall innerly forming a conical entryway, this conical entryway facilitating the insertion of said retaining portion of the anchoring member beyond said first collar until it enters into said retaining housing.

The invention will be well understood and other characteristics and advantages thereof will become apparent with reference to the appended schematic drawings illustrating two possible embodiments of the retaining system concerned as non-limiting examples.

For simplification, parts or elements reproduced from one embodiment to another are designated using the same reference numbers.

Figures 7, 8:
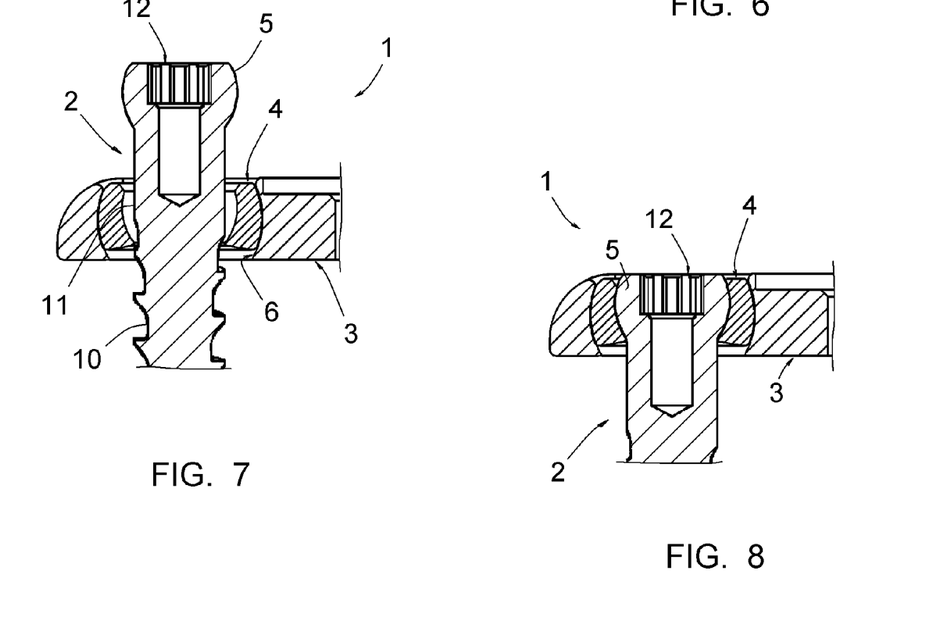
FIGS. 7 to 8 are views of the ring, of the bone plate and of a screw together forming the retaining system, during two steps for positioning of the screw.

FIGS. 7 and 8 illustrate a system 1 for retaining an anchor screw 2 on a bone plate 3 which, according to said first embodiment, comprises a retaining ring 4, a retaining portion 5 arranged on the screw 2 and a housing arranged in the plate 3.

The screw 2 comprises a threaded body 10 adapted to be placed in position in the bone of a vertebral body, a smooth cylindrical intermediate portion 11 and a head forming said retaining portion 5. The latter is in the shape of a sphere segment containing the equator of this sphere.

The screw 2 also comprises a proximal cavity 12 allowing its handling in rotation, which is star-shaped in the example of embodiment shown in the drawing.

The bone plate 3 is a metal plate in particular, intended to be fastened by means of several screws 2 to the vertebral bodies of two or three adjacent vertebrae to immobilise these vertebrae relative to one another. It comprises a plurality of holes for receiving screws 2 and rings 4, each of which forms a housing 6. This housing 6 is in the shape of a sphere segment which contains the equator of this sphere.

Figure 1:
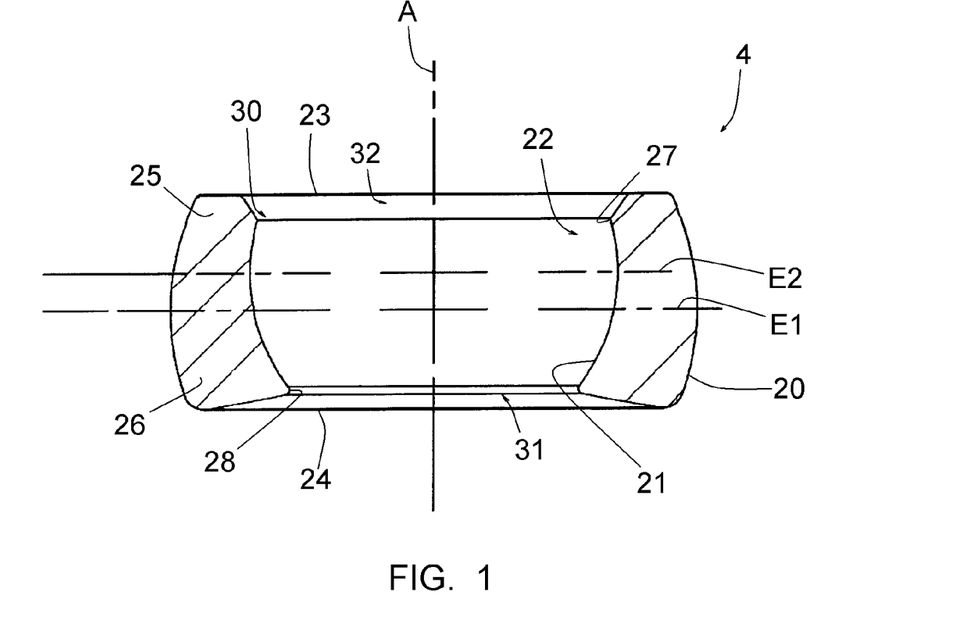
FIG. 1 is a cross-sectional view of a ring included in this retaining system according to a first embodiment.
Figure 2:
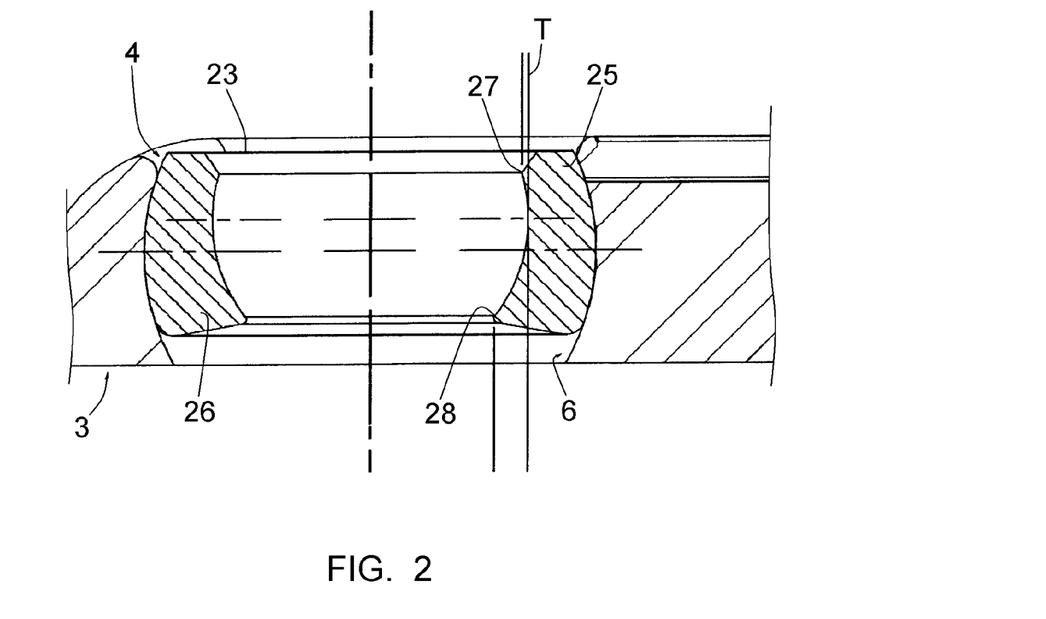
FIG. 2 is a similar view to FIG. 1, after placing in position on a bone plate.

The ring 4 is circular and with a continuous peripheral wall, and is made in a material that is slightly elastically deformable, in PEEK (polyetheretherketone) in particular or in high density polyethylene. As can be more clearly seen in FIGS. 1 and 2, it has an outer peripheral surface 20 in the form of a segment of a first sphere containing the equator of this first sphere, and an inner peripheral surface 21 in the form of a segment of a second sphere containing the equator of this second sphere.

Figures 3, 4, 5, 6:
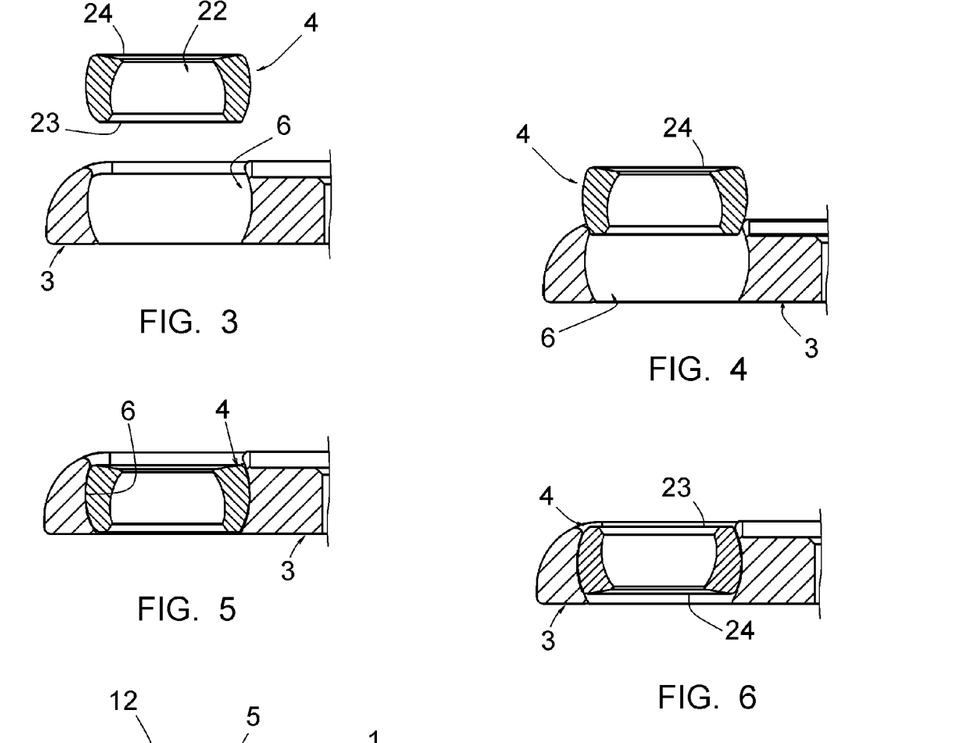
FIGS. 3 to 6 are views of the ring and of the bone plate at four steps for positioning the ring on the plate.

The respective diameters of the sphere generating the housing 6 of said first sphere are such that the ring 4 is able to take up position in fitted manner in this housing 6, as shown in FIG. 5, and can be retained therein with the possibility of multi-directional movements within this housing, in particular with the possibility of turning through 180° as can be seen by comparing FIGS. 5 and 6.

The ring 4 innerly delimits a housing 22 for retaining the retaining portion 5 provided in the screw 2. The respective diameters of the sphere generating the retaining portion 5 and of said second sphere are such that the retaining portion 5 is able to take up position in fitted manner inside this housing 22, as shown in FIG. 8.

The equator E2 of said second sphere is offset relative to the equator E1 of said first sphere along axis A of the ring 4, on the side of a first axial end 23 of the ring 4, which is the end via which the screw 2 is intended to be inserted through the ring 4.

The inner peripheral surface 21, between the equator E2 and the first end 23, forms a proximal portion of this surface 21 and, between the equator E2 and the second axial end 24 opposite the first end 23, forms a distal portion of this surface 21. Having regard to the above-mentioned offset of the equators E1 and E2, the extent of spherical closing of said proximal portion of the surface 21 is lesser than the extent of spherical closing of the distal portion of this surface 21; as a result said proximal portion of the surface 21, together with the outer peripheral surface 20, and on one side of the equator E2, delimits a proximal portion 25 of the ring 4 whose mean radial thickness is smaller than the mean radial thickness of the distal portion 26 extending on the other side of the equator E2.

In other words the wall of the ring 4, on the proximal side and at said first end 23, forms a first collar 27 whose dimension in the radial direction relative to a plane T tangent to said second sphere and perpendicular to the equator E2, is distinctly smaller than the dimension in the radial direction relative to this same plane T of the second collar 28 formed on the distal side at said second end 24 by the wall of the ring 4.

On the side of said first end 23, the inner peripheral surface 21 is interrupted so as to delimit a proximal opening 30 whose diameter is slightly smaller than the diameter of the retaining portion 5. On the side of said second end 24, the inner peripheral surface 21 is interrupted so as to delimit a distal opening 31 whose diameter is slightly larger than that of the intermediate portion 11 of the screw 2, and is distinctly smaller than the diameter of the retaining portion 5.

The mean radial thickness of the proximal portion 25 of the ring 4 is such that this proximal portion 25 is able to allow the forced passing of the retaining portion 5 when this retaining portion 5 is inserted in the housing 22, the resistance generated by this forced passing being insufficient however to hamper screwing of the screw. As a result this forced passing is achieved by mere continued screwing of the screw 2 after the arrival of the retaining portion 5 in contact with the first collar 27. On the other hand, the mean radial thickness of the distal portion 26, and the height and thickness of the second collar 28, are sufficient so that this distal portion 26 prevents the retaining portion 5 from passing through it, notwithstanding the slight degree of elastic deformation of the constituent material of the ring 4.

In addition, in the illustrated example, the ring 4 comprises a proximal conical entryway 32 facilitating the insertion of the screw 2 in the housing 22 of the ring 4.

The ring may in particular have the following dimensions:
diameter of said first sphere: 10 mm,
diameter of said second sphere: 7 mm,
offset of equator E2 relative to equator E1: 0.70 mm,
dimension of the first collar 27 in radial direction relative to plane T: 0.15 mm,
dimension of the second collar 28 in radial direction relative to plane T: 0.75 mm.

In practice, as shown in FIGS. 3 to 8, a ring 4 is presented opposite the housing 6 in which it is intended to be received, in a position turned through 180° C. relative to its position of use i.e. with its end 23 facing the plate 3 (FIG. 3). The deformability in the radial direction of the proximal portion 25 of the ring 4 allows radial contraction of the ring 4, permitting the forced passing of this ring into the proximal entryway of the housing 6 (FIG. 4) followed by retaining of this ring in this housing (FIG. 5), with the possibility of multi-directional movements.

The ring 4 is then turned through 180° to take up its position of use (FIG. 6).

The plate being placed in its implanting position, the screw 2 is then inserted through the ring 4 (FIG. 7) and is screwed until its retaining portion 5 takes up position inside the housing 22 (FIG. 8). As mentioned above, during this screwing operation, this retaining portion 5 comes to bear against the first collar 27 deforming it elastically in the radial direction, to allow the portion 5 to advance beyond this collar.

Figure 9:
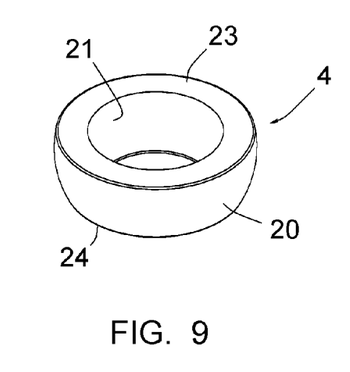
FIG. 9 is a perspective view of the ring according to a first variant.
Figure 10:
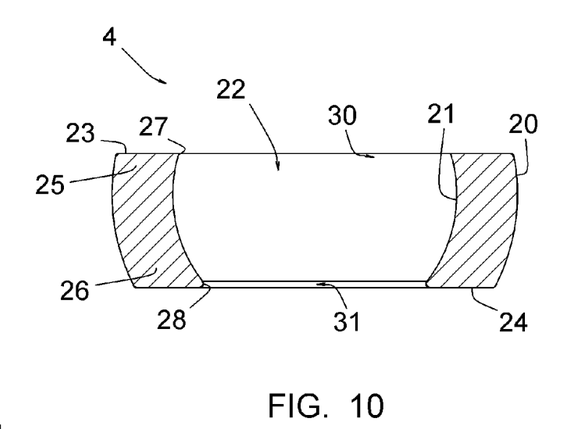
FIG. 10 is a cross-sectional view passing through the axis of this ring.

FIGS. 9 and 10 show a variant of embodiment of the ring 4, in which the equators of said first and second spheres are not offset from each other but on the contrary are merged. In this case, the ring 4, on the side of said first axial end 23, has a proximal portion 25 whose height is distinctly shorter than the distal portion 26 located on the side of said second axial end 24; in the same manner as previously, the inner peripheral surface 21 is interrupted so as to delimit, via a first collar 27, a proximal opening 30 whose diameter is slightly smaller than the diameter of the retaining portion 5, whilst on the side of the said second end 24, the inner peripheral surface is interrupted so as to delimit, via second collar 28, a distal opening 31 whose diameter is slightly larger than the diameter of the intermediate portion 11 of the screw 2 and is distinctly smaller than the diameter of the retaining portion 5.

Figure 11:
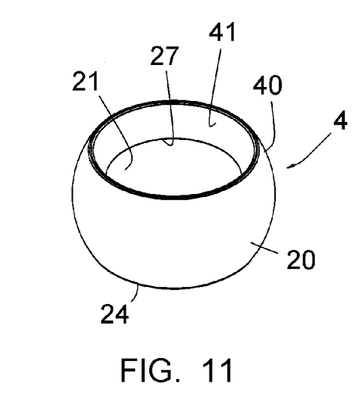
FIG. 11 is a perspective view of the ring according to a second variant.
Figure 12:
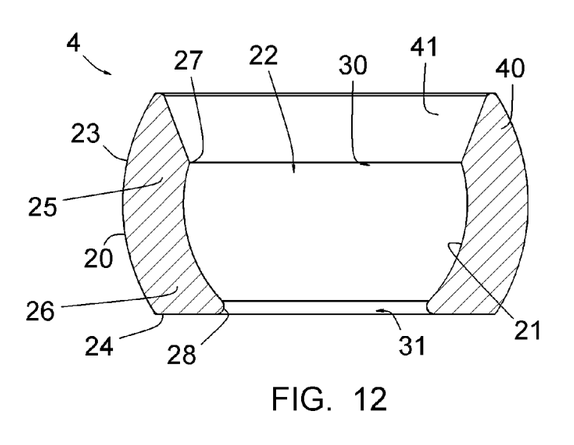
FIG. 12 is a cross-sectional view passing through the axis of this ring.

FIGS. 11 and 12 show another variant of embodiment of the ring 4, in which the equators of said first and second spheres are also merged. In this case the ring 4, beyond the end 23 delimiting the first collar 27, comprises a proximal extension wall 40 innerly forming a conical entryway 41. This conical entryway facilitates the insertion of the retaining portion 5 into the housing 22 delimited by the inner peripheral surface 21. For the remainder, the ring 4 is identical to the one shown in FIGS. 9 and 10.

Figure 13:
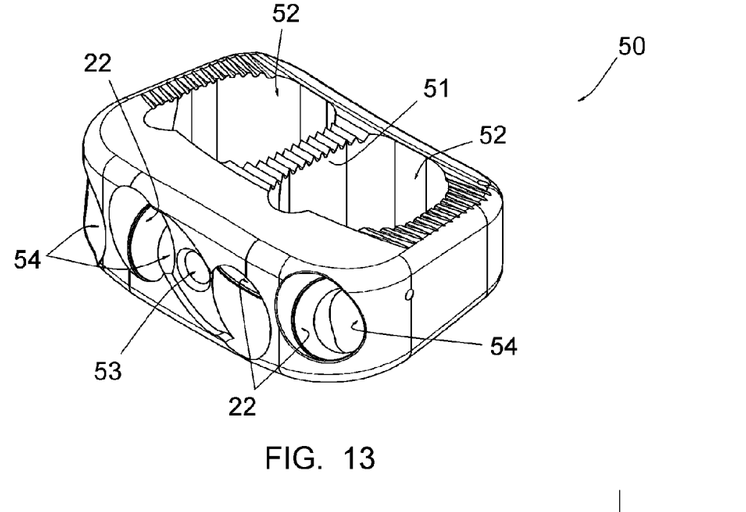
FIG. 13 is a perspective view of a cage including the retaining system according to a second embodiment.
Figure 14:
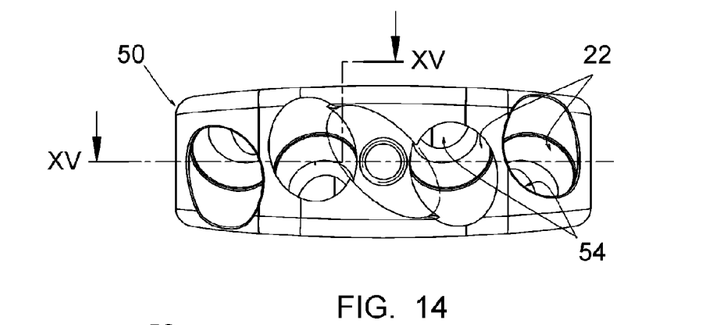
FIG. 14 is a side view of the cage from its proximal side.
Figure 15:
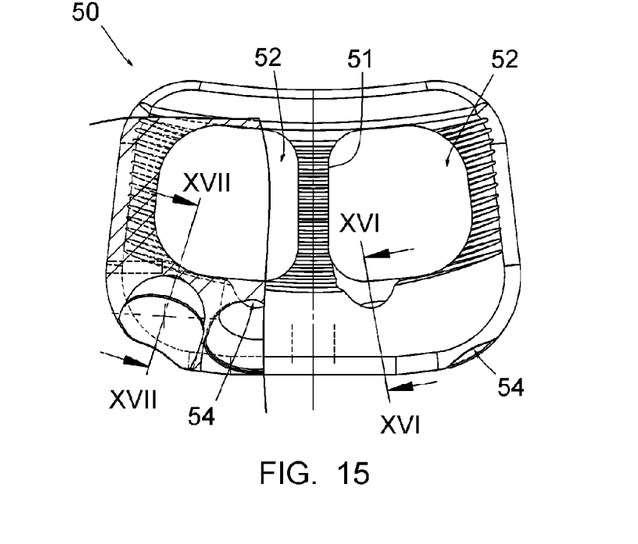
FIG. 15 is an overhead view of the cage, with partial cross-section along line XV-XV in FIG. 14.

FIGS. 13 to 15 show a second embodiment of the invention, in which the implantable part is an intervertebral cage 50 intended to be inserted between the vertebral bodies of two adjacent vertebrae.

This cage 50 has a peripheral wall and a median partition 51 delimiting two cavities 52 intended to receive bone grafts. It is in a mono-material i.e. made of a single material which is elastically slightly deformable. In particular the material is PEEK (polyetheretherketone).

On its anterior face, the cage 50 comprises a median hole 53 and an imprint for mounting thereof on the end of an impacting instrument, and four side holes 54 intended to receive screws (not illustrated but identical or very similar to the screw illustrated in FIGS. 7 and 8), these screws allowing the anchoring of the cage 50 to the vertebral bodies between which this cage is inserted. As can be seen in FIG. 14, the first and third holes 54 from the left in this figure are directed towards the top of the cage 50 and are intended to receive anchor screws in the body of the overlying vertebra, whilst the second and fourth holes 54 are directed towards the bottom of the cage 50 and are intended to received anchor screws in the body of the underlying vertebra.

Figure 16:
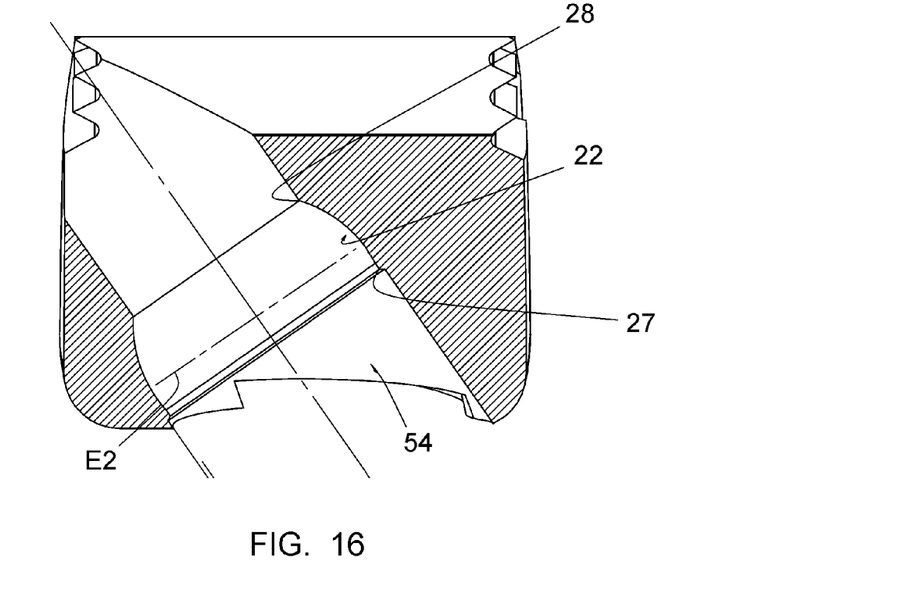
FIG. 16 is a cross-sectional view of the cage along line XVI-XVI in FIG. 15.
Figure 17:
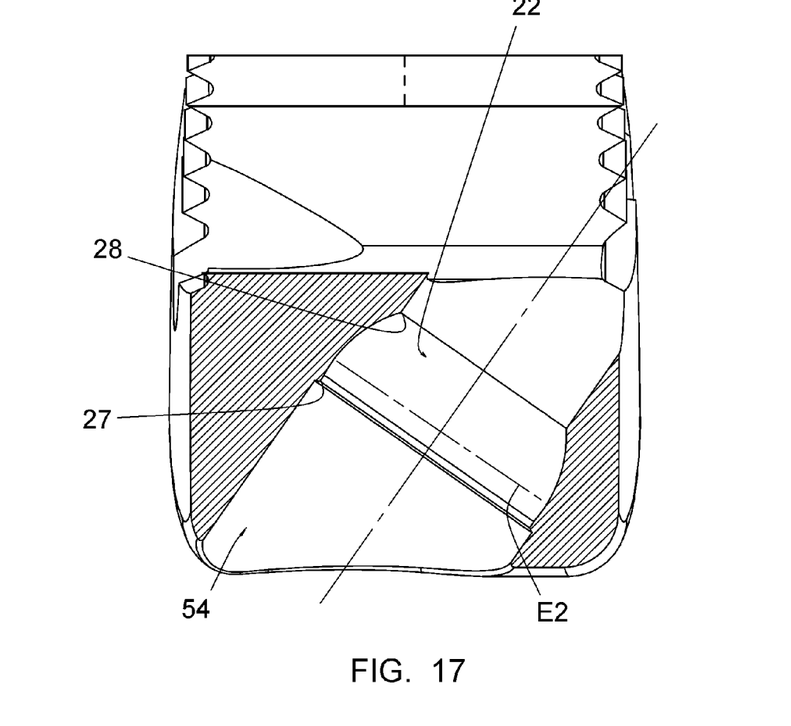
FIG. 17 is a cross-sectional view of the cage along line XVII-XVII in FIG. 15.

With reference to FIGS. 16 and 17, it can be seen that each hole 54 forms an anterior housing 22 forming a housing to retain the retaining portion 5 provided in a screw 2. The housing 22, and hence the retaining housing that it forms, has a first diameter at its anterior axial end which is the end via which the anchoring member is intended to be inserted through this retaining housing, and a second diameter, smaller than said first diameter, at its posterior axial end; the peripheral surface of the hole 54 delimiting this housing 22—between these first and second diameters—has a maximum diameter similar to E2 in the first embodiment, that is greater than said first diameter and said second diameter; this maximum diameter E2 on the side of said anterior axial end, delimits the first collar 27 capable of being elastically deformed which forms a continuous circular projection, and on the side of said posterior axial end delimits the said second collar 28 which cannot be elastically deformed by the retaining portion 5 provided in the screw 2.

As is apparent from the foregoing, the invention provides a system for retaining a screw 2 or other anchoring member on a plate 3 or other implantable part, having the determinant advantages of ensuring perfect retaining of the anchoring member relative to the implantable part, of not entailing any additional procedure other than the placing in position of the anchoring member on the implantable part, and of allowing the anchoring member to be oriented relative to the implantable part in the most suitable anchoring direction.

The invention has been described above with reference to embodiments provided as examples. It is evidently not limited to these embodiments but extends to all other embodiments covered by the claims appended hereto.

The invention claimed is:

1. System for retaining an anchoring member on an implantable part, comprising:
a system for retaining an anchoring member comprising:
an implantable part;
a retaining housing arranged in a part of the implantable part having a degree of elastic flexibility and delimited by a continuous wall of the part having the degree of elastic flexibility, the retaining housing being arranged directly in the wall of the implantable part, the retaining housing comprising:
a first axial end, via which the anchoring member is insertable through the retaining housing, and
a second axial end opposed to the first axial end;
a retaining portion arranged on the anchoring member, the retaining portion configured to be located at the retaining housing once the anchoring member has been placed in position, wherein:
the continuous wall forms, on the side of the first axial end, a first collar integral with the part, the first collar forming a first continuous circular projection capable of being elastically deformed by the retaining portion arranged on the anchoring member, the first circular projection formed by the first collar protruding radially and inwardly in the retaining housing and defining a first projection diameter;
the continuous wall is continuous from a top surface to a bottom surface of the retaining housing;
the retaining housing has a spherical shape and has a first diameter at said first axial end, a second diameter, smaller than the first diameter, at the second axial end, and a maximum diameter between said the diameter and second diameter, the maximum diameter being larger than the first diameter and second diameter, the continuous wall thus forming, on the side of said first axial end, the first collar;
the continuous wall also forms, on the side of said second axial end, a second collar forming a second continuous circular projection defining a second projection diameter, smaller than the first projection diameter, the second collar being not able to be elastically deformed by said retaining portion;
the retaining portion has a spherical shape having a maximum diameter substantially identical to the maximum diameter of the retaining housing, and is shaped so that it is able to follow the contour of this housing when the anchoring member is placed in position, the retaining portion therefore being capable of elastically deforming the first collar then of taking up a position in fitted manner inside the retaining housing, bearing against the second collar; and
the part having a degree of elastic flexibility is an elastically deformable material having a degree of deformability that is sufficient to allow, by elastic deformation, the passage of the retaining portion beyond said first collar,
wherein a thickness in the radial direction of the second collar is about five times larger than a thickness in the radial direction of the first collar.

2. System according to claim 1, wherein the maximum diameter is the equator of the sphere segment defining the retaining housing, and the equator is offset along the axis of the retaining housing on the side of the first end.

3. System according to claim 1, wherein the first end of the retaining housing is extended by a wall innerly forming a conical entryway, the conical entryway facilitating the insertion of the retaining portion of the anchoring member beyond said first collar until it enters into the retaining housing.

4. System according to claim 1, wherein the part having a degree of elastic flexibility is in PEEK material (polyetheretherketone).

5. System according to claim 1, wherein the wall of the retaining housing and a head portion of the anchoring member are not threaded.

6. System for retaining an anchoring member on an implantable part, comprising:
a system for retaining an anchoring member comprising:
an implantable part;
a retaining housing arranged in a part of the implantable part having a degree of elastic flexibility and delimited by a continuous wall of the part having the degree of elastic flexibility, the retaining housing comprising:
a first axial end, via which the anchoring member is insertable through the retaining housing, and
a second axial end opposed to the first axial end;
a retaining portion arranged on the anchoring member, the retaining portion configured to be located at the retaining housing once the anchoring member has been placed in position, wherein:
the continuous wall forms, on the side of the first axial end, a first collar integral with the part, the first collar forming a first continuous circular projection capable of being elastically deformed by the retaining portion arranged on the anchoring member, the first circular projection formed by the first collar protruding radially and inwardly in the retaining housing and defining a first projection diameter;
the retaining housing has a spherical shape and has a first diameter at said first axial end, a second diameter, smaller than the first diameter, at the second axial end, and a maximum diameter between said the diameter and second diameter, the maximum diameter being larger than the first diameter and second diameter, the continuous wall thus forming, on the side of said first axial end, the first collar;
the continuous wall also forms, on the side of said second axial end, a second collar forming a second continuous circular projection defining a second projection diameter, smaller than the first projection diameter, the second collar being not able to be elastically deformed by said retaining portion;
the retaining portion has a spherical shape having a maximum diameter substantially identical to the maximum diameter of the retaining housing, and is shaped so that it is able to follow the contour of this housing when the anchoring member is placed in position, the retaining portion therefore being capable of elastically deforming the first collar then of taking up a position in fitted manner inside the retaining housing, bearing against the second collar;
the part having a degree of elastic flexibility is an elastically deformable material having a degree of deformability that is sufficient to allow, by elastic deformation, the passage of the retaining portion beyond said first collar;
the retaining housing is arranged in a circular ring with a continuous peripheral wall extending around the entirety of the circular ring, an outer peripheral surface of the retaining housing being in the shape of a sphere segment containing the equator of the sphere; and a housing is arranged in the implantable part to receive the ring, the housing being shaped as a sphere segment containing the equator of the sphere, and having a diameter such that the ring is capable of taking up position in fitted manner inside the housing and of being retained inside the housing with possible multidirectional movements of the ring inside the housing, wherein a thickness in the radial direction of the second collar is about five times larger than a thickness in the radial direction of the first collar.

7. System according to claim 6, wherein the maximum diameter is the equator of the sphere segment defining the retaining housing, and the equator is offset along the axis of the retaining housing on the side of the first end.

8. System according to claim 6, wherein the first end of the retaining housing is extended by a wall innerly forming a conical entryway, the conical entryway facilitating the insertion of the retaining portion of the anchoring member beyond said first collar until it enters into the retaining housing.

9. System according to claim 6, wherein the part having a degree of elastic flexibility is in PEEK material (polyetheretherketone).

10. System according to claim 6, wherein the wall of the retaining housing and a head portion of the anchoring member are not threaded.

* * * * *